(12) United States Patent
Jackson et al.

(10) Patent No.: US 9,770,678 B2
(45) Date of Patent: Sep. 26, 2017

(54) SYNCHRONIZED VACUUM DEGASSING FOR LIQUID CHROMATOGRAPHY

(71) Applicant: Waters Technologies Corporation, Milford, MA (US)

(72) Inventors: Michael R. Jackson, Woonsocket, RI (US); Christopher Seith, Franklin, MA (US); Steven J. Ciavarini, Natick, MA (US); Kara O'Donnell, Watertown, MA (US); John Angelosanto, North Attleboro, MA (US); John Leason, Taunton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 314 days.

(21) Appl. No.: 14/687,290

(22) Filed: Apr. 15, 2015

(65) Prior Publication Data

US 2015/0298027 A1    Oct. 22, 2015

Related U.S. Application Data

(60) Provisional application No. 61/981,329, filed on Apr. 18, 2014.

(51) Int. Cl.
*B01D 19/00*    (2006.01)
*B01D 15/08*    (2006.01)
(Continued)

(52) U.S. Cl.
CPC ......... *B01D 19/0073* (2013.01); *B01D 15/08* (2013.01); *B01D 15/16* (2013.01); *B01D 19/0036* (2013.01); *B01D 19/0063* (2013.01); *B01D 19/0068* (2013.01); *G01N 30/14* (2013.01); *G01N 30/26* (2013.01); *G01N 30/34* (2013.01)

(58) Field of Classification Search
CPC . B01D 19/00; B01D 19/0036; B01D 19/0063
USPC ................ 95/241, 247; 96/155, 174, 193, 6
See application file for complete search history.

(56) References Cited

U.S. PATENT DOCUMENTS 7,947,112 B1 *  5/2011  Gerner ............... B01D 19/0063
                                                        210/640
2008/0006578 A1   1/2008  Sims et al.

FOREIGN PATENT DOCUMENTS

WO        2014002665 A1    1/2014

OTHER PUBLICATIONS

Combined Search and Examination Report in related UK Patent Application No. 1506288.8, mailed on Jan. 14, 2016; 6 pages.

* cited by examiner

*Primary Examiner* — Robert A Hopkins
(74) *Attorney, Agent, or Firm* — Schmeiser, Olsen & Watts LLP; William G. Guerin

(57) ABSTRACT

Described is a method for vacuum degassing of a liquid such as a solvent for a liquid chromatography system. The method includes modulating application of a vacuum to a fluid channel of a degasser so that each volume of a liquid drawn from the degasser experiences a residence time that is equal to the residence times of the other volumes. The residence time is determined as a time that the volume resides in the fluid channel under application of the vacuum and to a magnitude of the applied vacuum. The method is advantageous for use with liquid chromatography systems where differences in the diffusion rates of solvents into the degasser vacuum can otherwise introduce error into the composition gradient of a mobile phase.

17 Claims, 10 Drawing Sheets

(51) Int. Cl.
*B01D 15/16* (2006.01)
*G01N 30/26* (2006.01)
*G01N 30/14* (2006.01)
*G01N 30/34* (2006.01)

SYNCHRONIZED VACUUM DEGASSING FOR LIQUID CHROMATOGRAPHY

RELATED APPLICATION

This application claims the benefit of the earlier filing date of U.S. Provisional Patent Application Ser. No. 61/981,329, filed Apr. 18, 2014 and titled "Synchronized Vacuum Degassing for Liquid Chromatography," the entirety of which is incorporated herein by reference.

FIELD OF THE INVENTION

The invention relates generally to vacuum degassing systems such as those used in liquid chromatography. More particularly, the invention relates to a method for degassing that reduces adverse effects due to differential diffusion rates of liquids during vacuum degassing.

BACKGROUND

Conventional vacuum degassing systems used for liquid chromatography are typically maintained at a constant vacuum level through use of a vacuum pump operating at a constant speed (revolutions per minute), operating by means that utilize feedback control or by cyclically applying a vacuum. The duration for which a solvent is present in the degasser is typically not constant due to changes in the flow rate of the solvent. Different types of solvents typically diffuse through the wall of the fluid channel within the degasser at different rates. Consequently, the different diffusion rates can adversely affect the measurement data obtain by the liquid chromatography system, for example, by introducing error to the composition gradient of a mobile phase.

SUMMARY

In one aspect, a method of vacuum degassing of a liquid includes modulating an application of a vacuum to a fluid channel of a degasser so that, for a plurality of volumes of a liquid drawn from the degasser, each volume of the liquid has a residence time that is equal to a residence time of each of the other volumes of the liquid. The residence time for each of the volumes of the liquid is responsive to a time that the volume of the liquid resides in the fluid channel under application of the vacuum and to a magnitude of the vacuum.

In another aspect, a system for vacuum degassing of a liquid includes a degasser, a vacuum source and a processor. The degasser has a fluid channel to conduct the liquid. The vacuum source is in communication with the degasser and is configured to apply a vacuum to the fluid channel. The processor is configured generate a control signal to modulate the application of the vacuum to the fluid channel of the degasser. For volumes of a liquid drawn from the degasser, each volume has a residence time that is equal to a residence time of each of the other volumes. The residence time for each of the volumes of the liquid is responsive to a time that the volume of the liquid resides in the fluid channel under application of the vacuum and to a magnitude of the vacuum.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

In brief overview, the invention relates to a method for vacuum degassing of a liquid. The method includes modulating a vacuum applied to a fluid channel of a degasser so that each volume of liquid drawn from the fluid channel of the degasser, the residence time for that volume is the same as the residence time for other volumes of the liquid drawn from the degasser regardless of the flow rate of the liquid or the volume of the drawn liquid. The residence time for a volume of liquid is determined as the time that the volume of the liquid resides in the fluid channel under application of the vacuum and to a magnitude of the vacuum. As used herein, the magnitude of the vacuum means the difference in pressure from ambient pressure. In particular, a lower pressure is considered to be a greater magnitude of vacuum. The method is particularly advantageous for applications in low pressure gradient formation where two or more liquids are combined into a single flow, such as a gradient mobile phase for liquid chromatography.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

Figure 1:
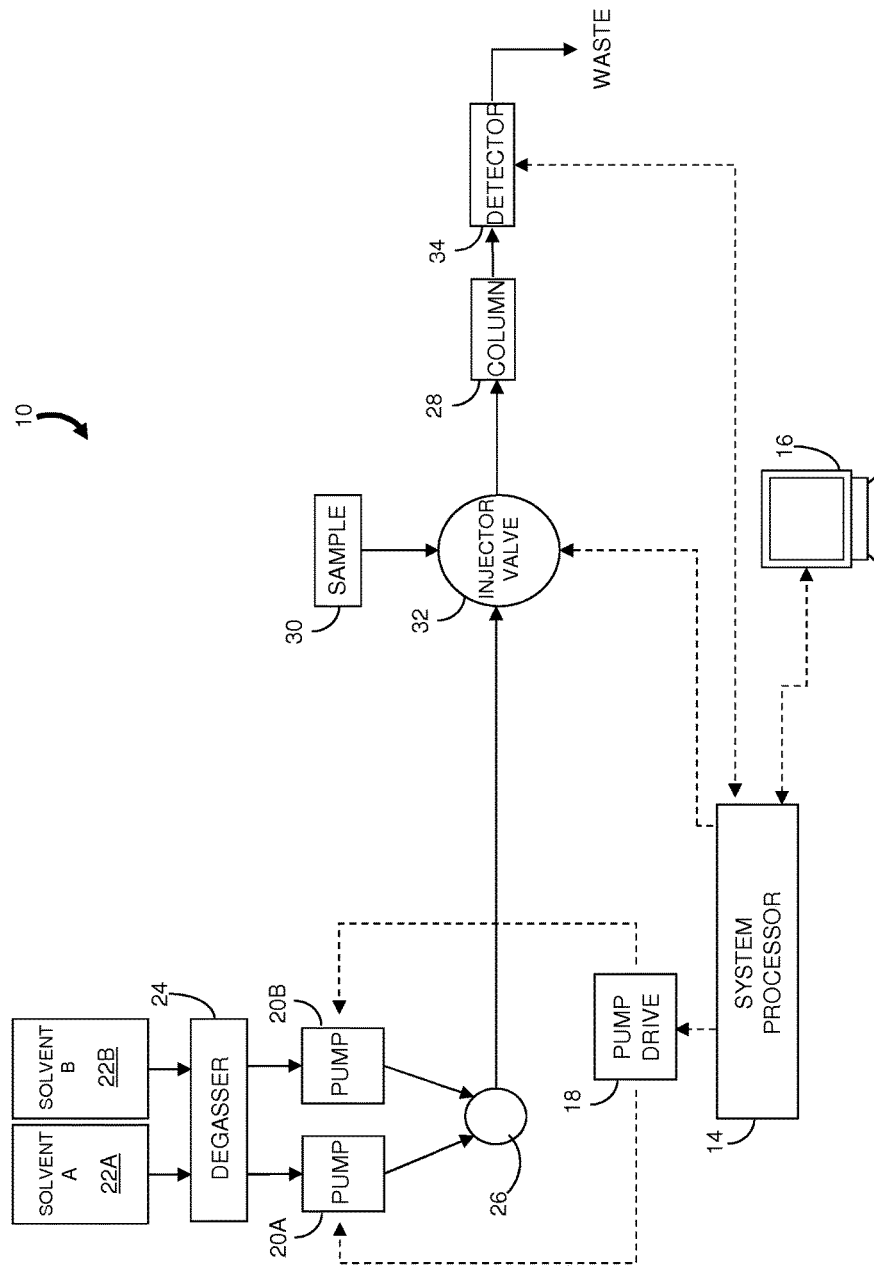
FIG. 1 is a block diagram of a liquid chromatography system configured for operation with a gradient mobile phase.

FIG. 1 is a block diagram of a liquid chromatography system 10 that includes a system processor 14 (e.g., microprocessor and controller) in communication with a user interface device 16 for receiving input parameters and displaying system information to an operator. The system processor 14 communicates with a pump drive module 18 for controlling operation of a pair of solvent pumps 20A and 20B. The pump 20 can include pump heads that may be configured in a variety of ways. For example, each pump 20 can include a primary pump head in serial communication with an accumulator pump head.

Solvent reservoirs 22A and 22B hold solvents A and B, respectively, to be combined in a binary gradient mobile phase. The solvent reservoirs 22A and 22B are in fluidic communication with inlets of a degasser 24 and the corresponding outlets of the degasser 24 are in fluidic communication with the inlets of the solvent pumps 20A and 20B, respectively. Although not shown, the degasser 24 is in communication with a vacuum source, such as a vacuum pump, to enable the fluid channels that conduct the solvents through the degasser 24 to be exposed to a vacuum environment. The degasser 24 removes dissolved gases in the solvents drawn from the reservoirs 22. The outlet of each pump 20 is in fluidic communication with an input port of a cross-connection 26 where the two solvents are combined as a binary mobile phase to be delivered to a chromatographic column 28.

A sample from a sample reservoir, or sample container, 30 can be injected into the mobile phase upstream from the chromatographic column 28 using an injector valve 32. The chromatographic column 28 is coupled to a detector 34 which provides a signal to the system processor 14 that is responsive to components in the sample as they elute from the system 10.

During operation of the liquid chromatography system 10 with the gradient mobile phase, the pumps 20 draw solvents from the reservoirs 22. The relative contributions of the solvents present in the mixed mobile phase depend on the flow rates of the pumps 20. The flow rate for each pump 20 changes in time during the gradient process according to a predetermined gradient composition for the mobile phase.

Figure 2:
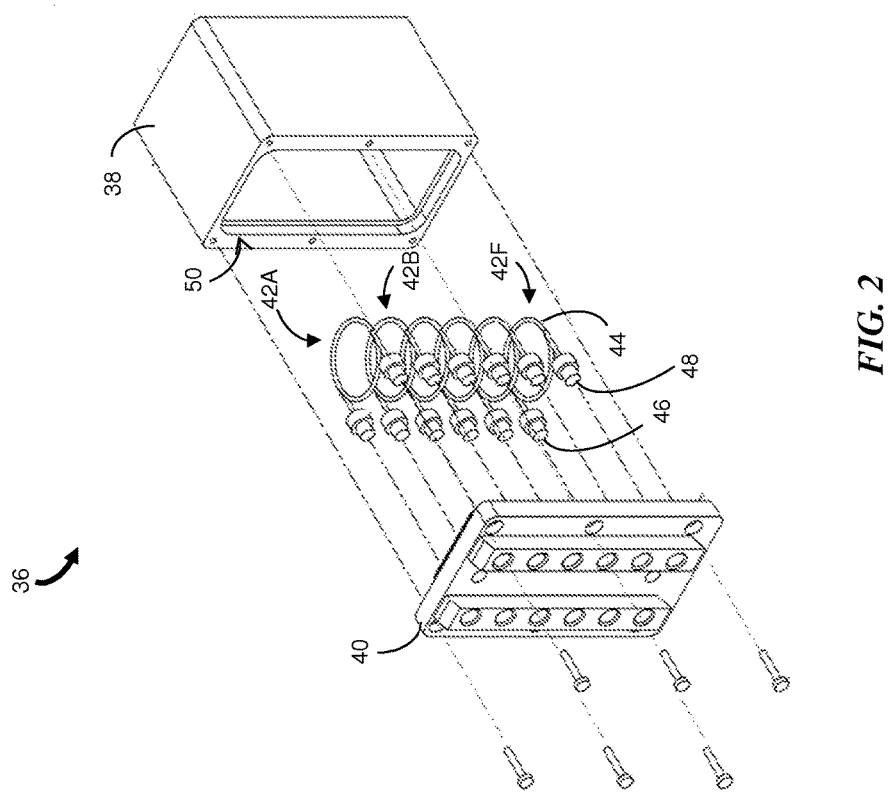
FIG. 2 is an exploded view of a degasser that can be used to degas multiple solvents in a liquid chromatography system.

FIG. 2 is an exploded view of a degasser 36 which may be used, for example, as the degasser 24 in FIG. 1. The illustrated degasser 36 includes a rear cover 38, a front manifold 40 and a number of tube assemblies 42A to 42F. Each tube assembly 42 includes a tube 44 having a first connector 46 for coupling to a fluid channel to receive a solvent and a second connector 48 for coupling to another fluid channel that receives the solvent after passing through the degasser 36. A seal or gasket (not shown) is used between the front manifold 40 and the adjacent surface 50 of the rear cover 38 to seal the vacuum region of the degasser 36 from the ambient environment.

Each tube 44 is formed of a permeable material such as polytetrafluoroethylene (e.g., Teflon® AF) through which components of a contained liquid diffuse when the tube 44 is subject to a vacuum environment. The tubes 44 are shaped into coils each having one or more loops. Each tube 44 has an inner volume defined by the inner diameter of the tube wall and the tube length between the connectors 46 and 48. One or more of the tubes 44 are used for degassing solvents, such as solvents A and B in FIG. 1, for a mobile phase. One or more tubes 44 may be used for wash solvents. The lengths, diameters and inner volumes of the tubes 44 may be the same or may have different values.

During operation of the degasser 36, at least a portion of the gases dissolved in the solvent within a tube 44 diffuse through the tube wall along with some of the solvent. The removal of gas from the solvent to a level less than saturation results in improved operation at downstream components of the liquid chromatography system. For example, if the solvents are not degassed, bubbles may form in the mobile phase which can lead to significant noise in measurement data. In one specific example, bubbles can interfere with the nebulization process at the input to a mass spectrometer detector, thereby acting as a source of measurement noise.

When a tube 44 is in a vacuum environment and contains a mixture of liquids, the liquids typically diffuse through the tube wall and into the vacuum at different rates. Consequently, the composition ratio of the liquids in the mixture that remains in the tube 44 changes over time while the tube 44 remains under vacuum. For example, if a solvent includes a modifying agent or buffering agent, an increase in the time that the solvent is under vacuum inside the degasser (i.e., the "residence time") can result in a relative enrichment of the modifying agent. The enrichment is the result of the solvent diffusing through the tube wall at a substantially greater rate than the modifying agent. The situation is further complicated if the flow rate of the solvent pump is not constant because the degree of enrichment will not remain constant.

The liquid volume capacity and length of each tube 44 and the flow rate of the passing solvent affect the residence time for a volume of the solvent inside the degasser 36. Thus changes in the flow rates of the different solvents present in the tubes 44 can significantly affect the changes in the relative contributions of the solvents to a gradient mobile phase.

Figure 3:
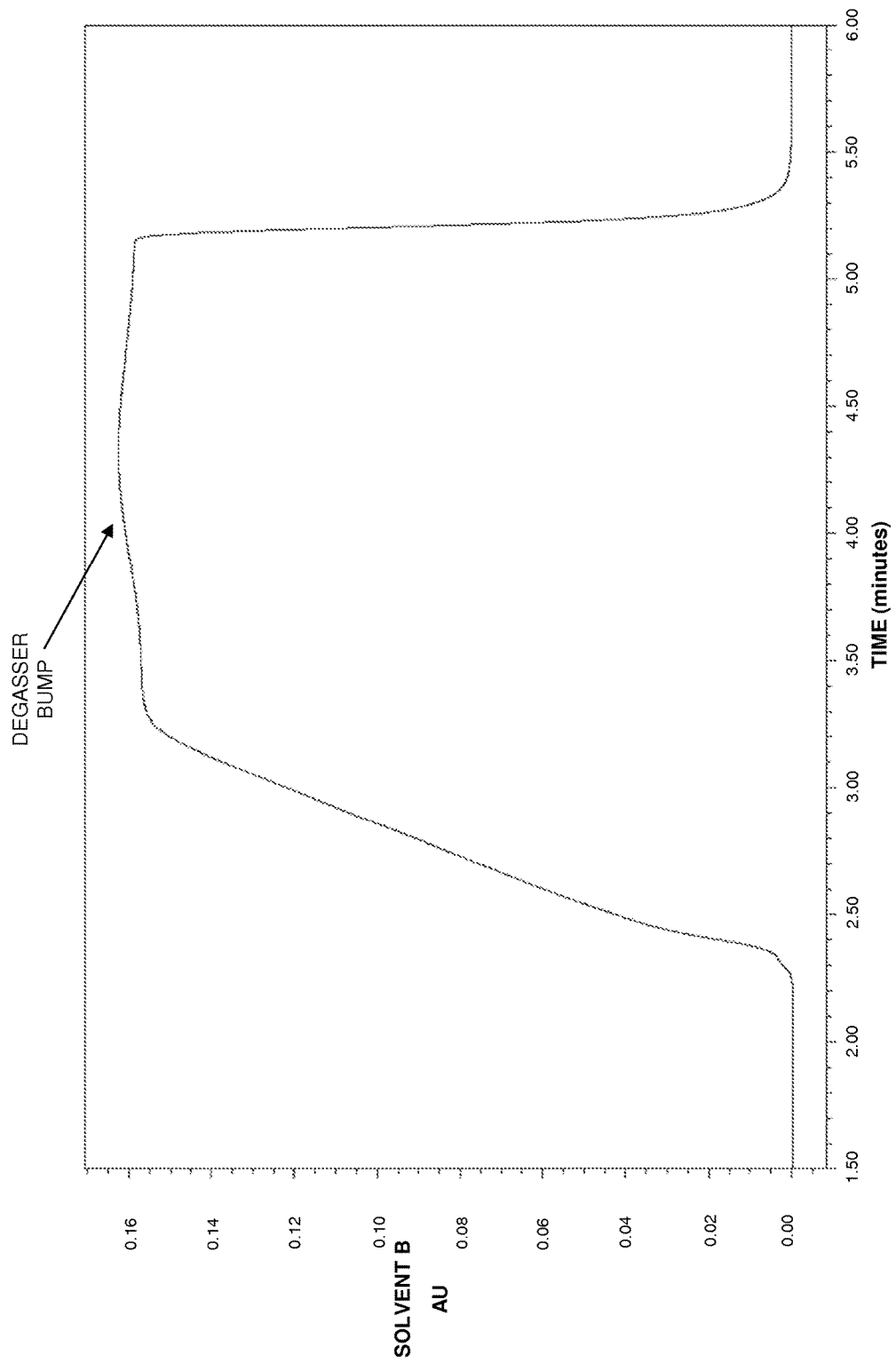
FIG. 3 shows a gradient composition profile having a degasser bump caused by mobile phase solvents having different degasser diffusion rates.

FIG. 3 shows a gradient composition profile for a mobile phase gradient comprised of two solvents: solvent A and solvent B. The profile indicates the relative amount of solvent B present in the mobile phase. For this profile, the relative contribution of solvent B to the mobile phase is commanded to linearly change from 0% to 100% with a concurrent reduction in the relative contribution of solvent A from 100% to 0%. After achieving a 100% relative concentration of solvent B, a small increase for a limited time is evident in the form of a "degasser bump" to what otherwise is expected to be a flat upper limit at a relative contribution of 100%. This degasser bump is due to the difference in diffusion rates described above and results in an apparent concentration of solvent B that exceeds 100%.

Figure 4:
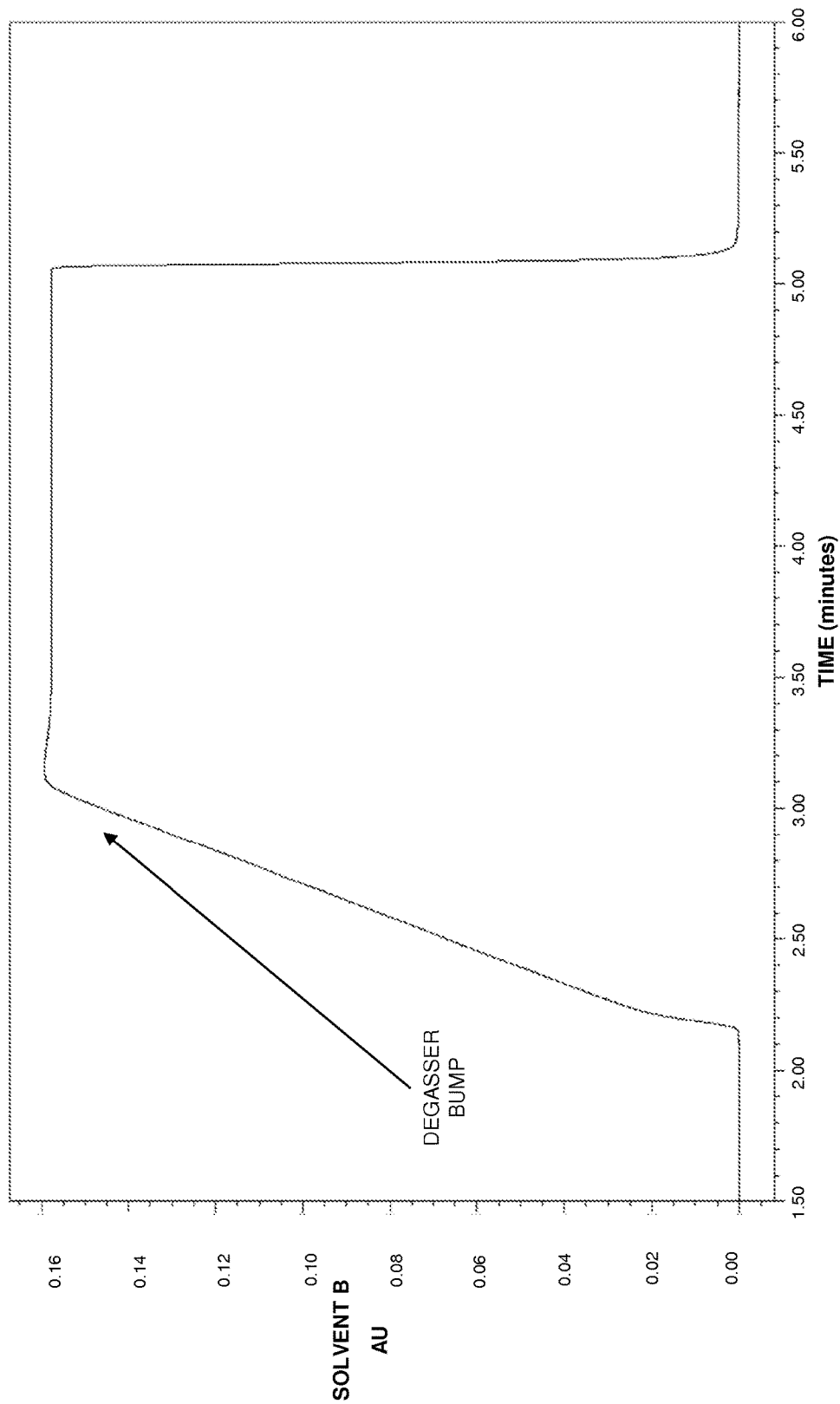
FIG. 4 shows another gradient composition profile having a degasser bump caused by mobile phase solvents having different degasser diffusion rates.

FIG. 4 similarly shows how different diffusion rates can result in a degasser bump in a gradient mobile phase. In this instance, the position and magnitude of the degasser bump along the gradient profile are different due to a change to flow rates that are less than the flow rates for the profile shown in FIG. 3. Slower flow rates generally result in a degasser bump that is present at some position along the linear ramp portion of the gradient profile.

Figure 5:
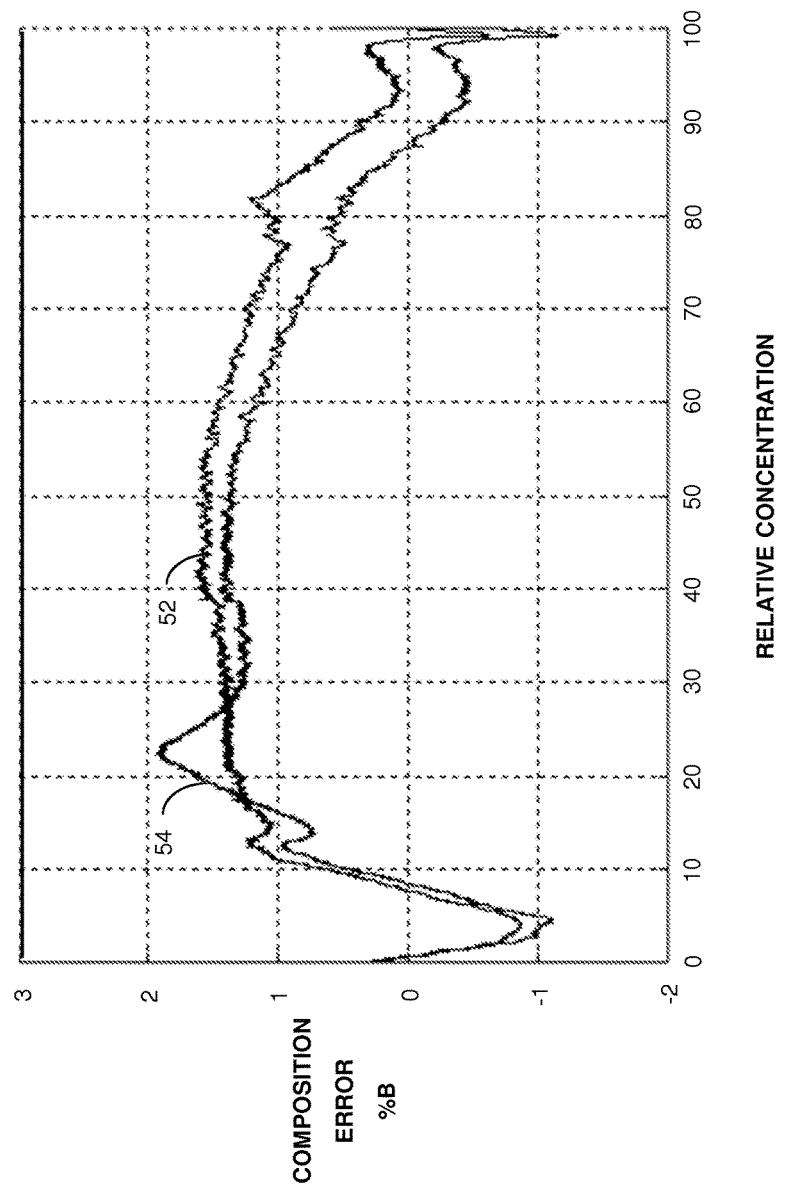
FIG. 5 is a graphical depiction of percentage composition errors in a gradient composition profile for a liquid chromatography system configured with and without a degasser.

FIG. 5 is a graphical representation of an error in a gradient composition profile where the relative concentration of solvent B changes linearly in time from 0% to 100%. Plot 52 shows the percentage error in the contribution of solvent B relative to the desired relative contribution value that occurs when no degasser is used. Plot 54 shows the error in the contribution of solvent B relative to the desired contribution value that occurs with the degasser. A significant bump occurs over a range from approximately 20% to 25% relative concentration of solvent B.

On low flow rate pumps for nano-scale operation, for example, with flow rates on the order of one microliter per minute, the residence time of a solvent in the degasser 36 is increased. Consequently, the adverse effects described above are more pronounced. In some instances, the result is excess contribution of one component which can cause distortion of chromatographic peaks and changes in retention times.

Referring again to FIG. 1, to deliver the solvent to the chromatographic system, the intake strokes of each pump 20 are coordinated. A single nano-pump intake stroke is executed to draw a portion of the respective solvent resident inside the degasser 24 toward the pump 20. Each solvent is delivered at a desired flow rate from the pump 20 to the cross connection 26 in the liquid chromatography system 10. Subsequent intake strokes draw additional solvent from the degasser 24 to the pump 20. Under typical operation, a fixed volume of solvent is drawn for each pump intake stroke.

By way of non-limiting numerical examples, a degasser fluid channel 44 (see tube 44 in FIG. 2) having a length of 18 in. and an inner diameter of 0.045 in. can have a total liquid volume capacity of approximately 470 µL. For a nano-flow liquid chromatography system utilizing a pump having a 50 µL intake stroke volume and delivering at flow rates from 0.2 µL/min to 100 µL/min, the residence times for a pump intake stroke range from several minutes to tens of hours. These residence times are significant in comparison to residence times for liquid chromatography systems configured for higher flow rates, where residence times typically range from a few seconds to approximately an hour.

Figure 6B:
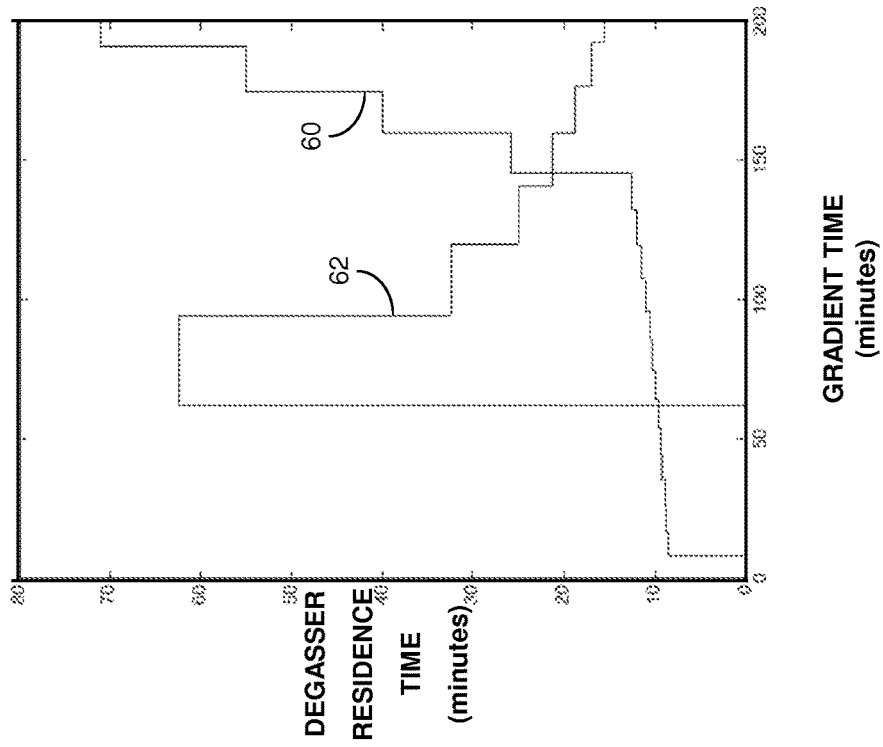
FIG. 6A is a graphical depiction of the flow rates of two solvents for a binary gradient mobile phase in a nano-scale liquid chromatography system and FIG. 6B is a graphical depiction of the residence time for each solvent in a degasser according to a conventional degassing technique.
Figure 6A:
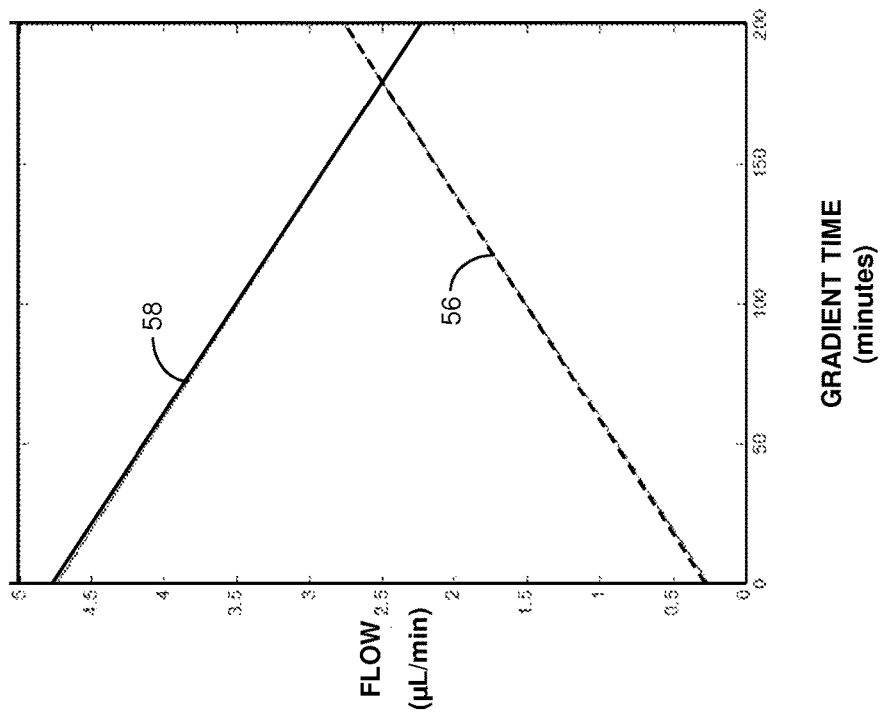

FIG. 6A depicts the flow rates of two solvents A and B contributing to a binary gradient mobile phase in a nano-scale liquid chromatography system. The relative contribution 56 of solvent B increases over time from 5% TO 55% while the relative contribution 58 of solvent A 58 decreases over time. FIG. 6B illustrates an example of the residence time in a degasser according to a conventional degassing of the solvents. The residence time 60 for solvent A is lower during the higher flow rate period in the early portion of the gradient mobile phase and then is substantially increased at later times. Conversely, the residence time 62 for solvent B is substantially greater early in the process when the flow rate of solvent B is low. Subsequently, the residence time 62 decreases significantly when the flow rate for solvent B increases.

It will be appreciated in light of the above description above that the substantial variations in degasser residence times shown in FIG. 6B can lead to errors in the composition gradient of the mobile phase.

In various embodiments of a method for vacuum degassing of a liquid described below, the residence time of a volume of liquid in a degasser is held constant. Thus the diffusion loss of liquid through the tube wall inside the degasser is maintained substantially constant for the volume of liquid regardless of the pump flow rate.

Figure 7:
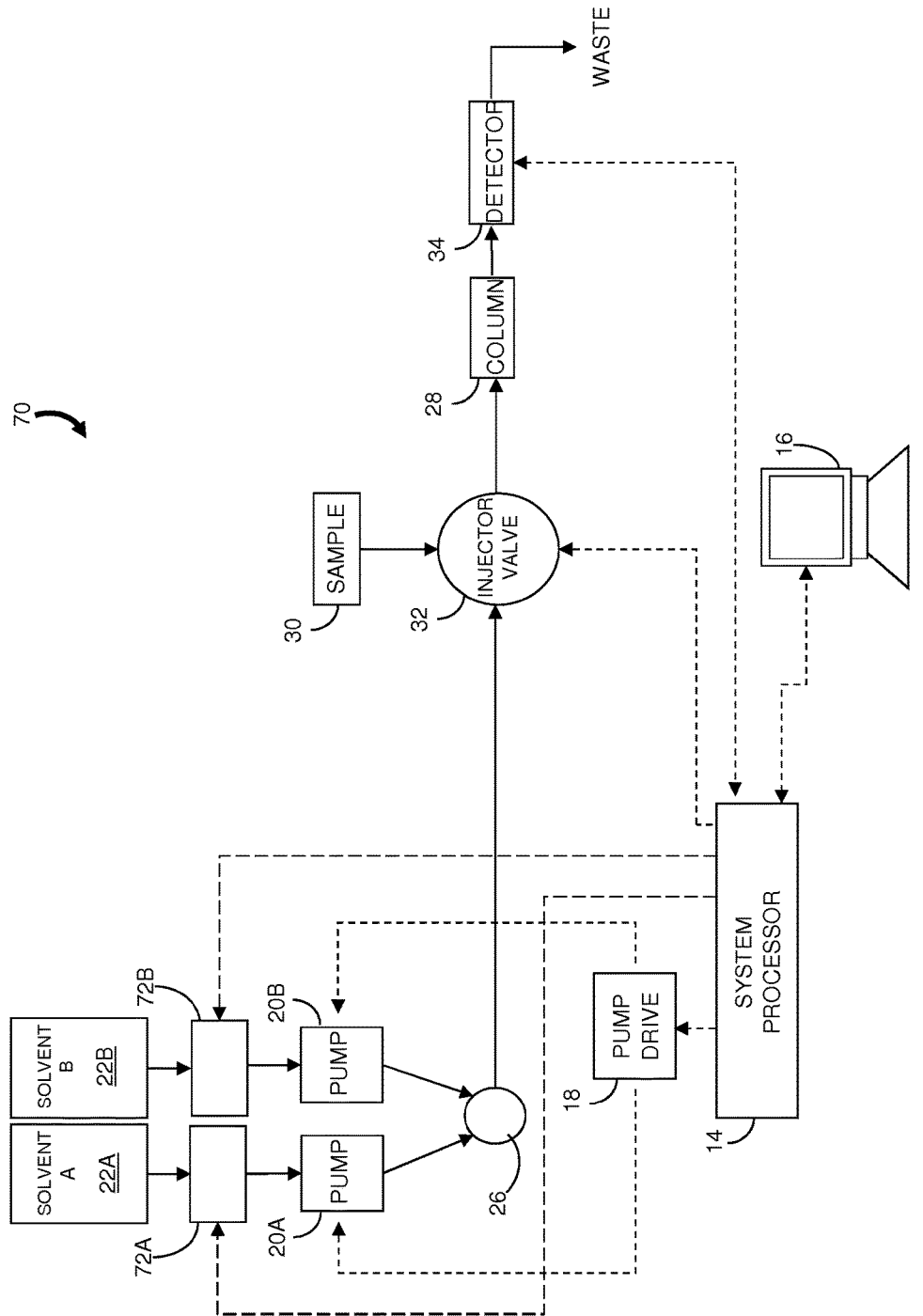
FIG. 7 is a block diagram of a liquid chromatography system that can be used to practice embodiments of a method for vacuum degassing of a liquid.

FIG. 7 is a block diagram of a liquid chromatography system 70 that can be used to practice embodiments of the method. The liquid chromatography system 70 is configured similarly to the liquid chromatography system 10 shown in FIG. 1; however, two independently controllable degassers 72A and 72B are used to degas solvents A and B, respectively. If the two degassers 72 are independently controlled according to the method, the degasser residence times of the solvents A and B can be maintained at a constant value throughout the gradient mobile phase.

Figure 8:
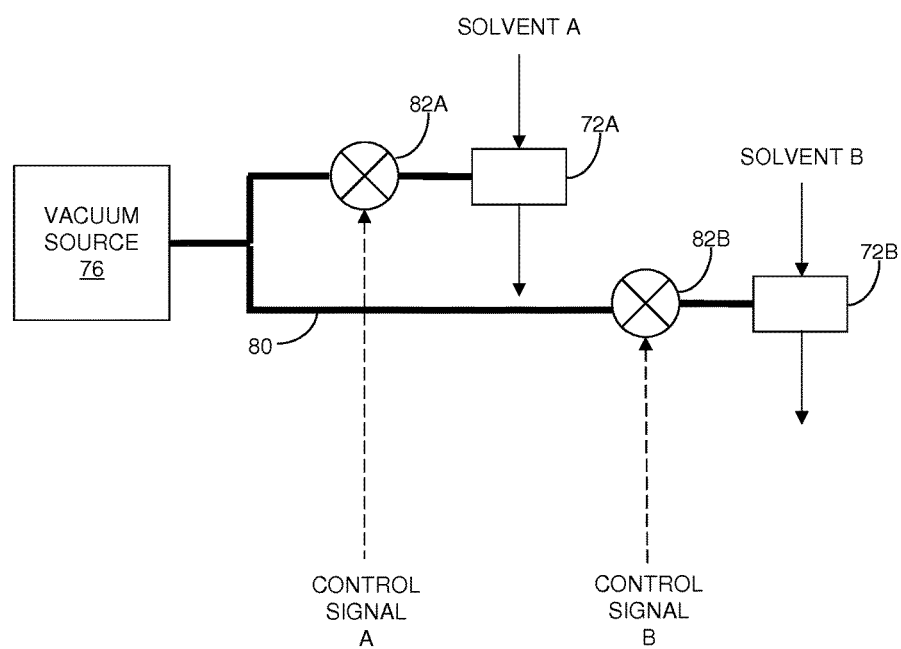
FIG. 8 is a block diagram of one configuration for the two degassers of FIG. 7.

FIG. 8 shows a block diagram of how the combination of the two degassers 72 of FIG. 7 may be configured. Each degasser 72 communicates with a single vacuum source 76 through a vacuum line 80 having a branch configuration, although in other embodiments the degassers 72 may communicate with separate vacuum sources. Each branch of the vacuum line 80 includes a vacuum valve 82A or 82B that is controlled to be in an open or a closed state according to a respective control signal.

Figure 9:
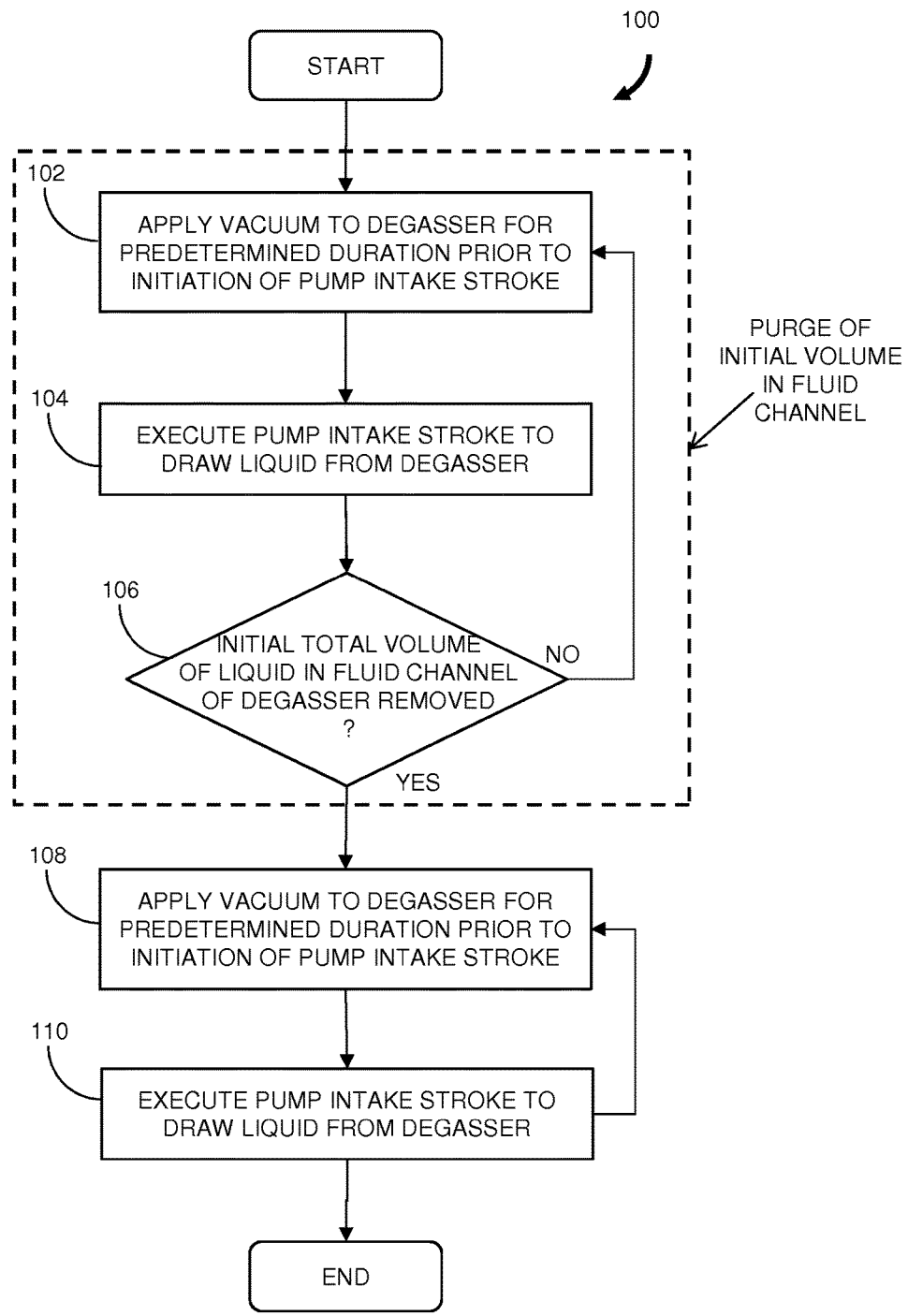
FIG. 9 is a flowchart representation of an embodiment of a method for vacuum degassing of a liquid.

In one embodiment of the method 100 for vacuum degassing of a liquid as shown in the flowchart of FIG. 9, the application of vacuum to the degassers is correlated to pump intake strokes. The illustrated embodiment is particularly advantageous for liquid chromatography systems utilizing nano-scale pump systems where the volume of solvent used during a chromatographic run is a small fraction of the total volumes of solvent present in the degassers.

The method 100 includes applying (102) a fixed vacuum level (i.e., a fixed vacuum magnitude) to a degasser for a fixed duration prior to initiation of each pump intake stroke when the pump intake stroke draws (step 104) solvent from the degasser. This process is repeated for a number of occurrences of a pump intake stroke. After determining (step 106) that a sufficient number of pump intake strokes have occurred to draw out (i.e., purge) the initial volume of solvent in the fluid channel inside the degasser, a subsequent sequence of vacuum application (step 108) and pump intake strokes (step 110) are used to supply the solvent, for example, for an intended purpose such as for a liquid chromatography measurement run. The volume of solvent drawn each time step 110 is performed will have the same residence time. The initial cycling process through steps 102 and 104 can be included as part of a priming function to be performed after a liquid chromatography system has been idle for a prolonged period or upon a change of solvents.

Modulation of the application of vacuum to a degasser is accomplished by actuating (opening) and deactuating (closing) a respective inline vacuum valve in accordance with control signals. Actuation of the valve results in application of the vacuum to the degasser. The pressure inside the degasser increases to a greater value, such as atmospheric pressure, when the valve is deactuated. The control signal used to actuate and deactuate the vacuum valve can be an electrical signal provided by a processor and controller module such as the system processor 14 of FIG. 7. Alternatively, the vacuum modulation can be achieved using other types of control signals and other forms of vacuum valves that may be configured for mechanical actuation or other types of actuation.

In some liquid chromatography systems, the pumps may be operated so that the volume of solvent drawn during a pump intake stroke changes over time during a gradient mobile phase. According to an alternative embodiment of the method, vacuum is applied to a degasser in advance of each intake stroke; however, the duration of the applied vacuum is proportional to the volume of solvent drawn from the degasser by the pump during an intake stroke. Thus the residence time for a unit volume of solvent is maintained constant throughout the duration of the mobile phase gradient.

Figure 10:
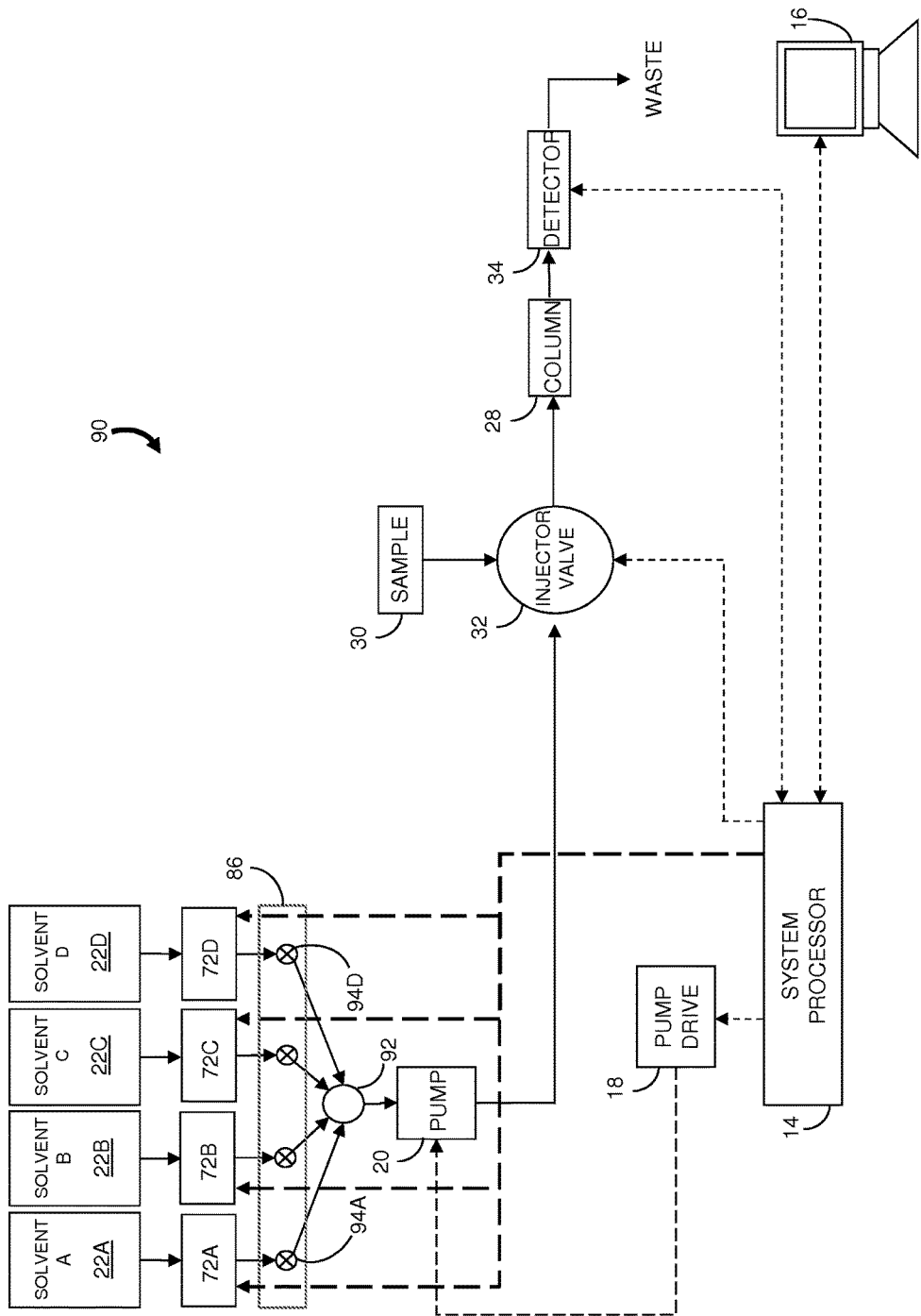
FIG. 10 is a block diagram of a liquid chromatography system that can be used to practice embodiments of a method for vacuum degassing of a liquid.

In liquid chromatography systems utilizing a low pressure gradient formation technique, the volume of solvent drawn from a degasser during a pump stroke can be a fraction of the total volume of solvents drawn by a pump. For example, FIG. 10 shows a block diagram of a liquid chromatography system 90 that includes four solvent reservoirs 22 each in communication with an independently controlled degasser 72. The degasser outlets are coupled to a gradient proportioning valve (GPV) 86 which is in communication with a cross-connection 92. The individual switching valves 94 of the GPV 86 are modulated to provide contributions of the four solvents in serial fashion to the cross-connection 92 where all the contributions are combined into a single liquid flow drawn through a single pump 20.

During operation, the four solvents can contribute to the total volume of liquid drawn by the pump 20. The actuation times of the switching valves 86 during a pump intake stroke define the volume contributions for each solvent and the relative contribution of each solvent to the pump stroke volume.

In one embodiment of the method, vacuum is applied to each degasser 72 in advance of each intake stroke. The duration of the vacuum applied to a particular degasser 72 is proportional to the volume of solvent drawn from the degasser 72 by the pump 20 during an intake stroke. In the previously described embodiment, the duration is directly proportional to the pump stroke volume because each pump 20 (see FIG. 7) only draws a single solvent. In this embodiment, the duration of the vacuum applied to a degasser 72 is proportional to the volume of the respective solvent that is drawn from the degasser during the pump stroke. Consequently, the duration for each degasser 72 is proportional to a respective fractional contribution of the corresponding solvent to the total pump stroke volume. Thus the residence time for a unit volume of solvent from each of the degassers 72 is maintained constant throughout the duration of the mobile phase gradient.

According to another embodiment of the method, the duration of a vacuum applied to the degasser at a fixed vacuum level is modulated in time according to the flow rate of the solvent. For example, the application of the vacuum may follow a square wave modulation where the duty cycle of the square wave is proportional to the flow rate. More specifically, the duration of the "pulses" of applied vacuum increase with increasing flow rate and, conversely, decrease as the flow rate decreases.

In another embodiment, the magnitude of the vacuum, or vacuum level, of a continuously applied vacuum is varied according to the flow rate of the solvent. For example, a weaker vacuum (i.e., higher pressure) is used for a lower flow rate while a stronger vacuum (i.e., lower pressure) is used for a higher flow rate. As long as each pump intake stroke acquires the same volume of solvent, the vacuum level can be correlated to the frequency of the pump intake strokes. If the flow rate of a pump is increased, and therefore the frequency of intake strokes increased, the vacuum level is increased (relative pressure decreased) inside the degasser. Conversely, if the flow rate of the pump is decreased, and therefore the frequency of intake strokes decreased, the vacuum level is decreased (relative pressure increased). This analog modulation of the vacuum level can be accomplished by controlling a variable-open vacuum valve disposed in the vacuum line leading to each degasser. For each degasser, a vacuum level sensor may be disposed between the degasser and the vacuum valve as part of a feedback control system used to establish the desired vacuum level.

In some embodiments of a synchronized degassing system, the use of controllable vacuum valves allows operation using a single vacuum pump to control multiple degassers. In alternative embodiments in which inline vacuum valves are not used, the modulation of the vacuum applied to a degasser is achieved by controlling the vacuum pump speed; however, this type of modulation requires a separate vacuum pump for each degasser and can be limited by the ability of each vacuum pump to change speed rapidly enough to attain the desired vacuum modulation waveform.

In the various embodiments of the method using synchronized vacuum degassing as described above, it is preferable to perform a purge of solvent lines prior to performing a chromatographic run. This purge process is desirable if there is significant time between operations of the liquid chromatography system, for example, several hours or days between operations. The residence time for the solvents within the degassers and the impact of the extended time on the degassing process are rendered moot by the purge process and liquid drawn from the degassers on each pump intake stroke subsequent to the purge will have acquired the required residence time.

While the invention has been shown and described with reference to specific embodiments, it should be understood by those skilled in the art that various changes in form and detail may be made therein without departing from the spirit and scope of the invention as recited in the accompanying claims. For example, although the embodiments of the method described above primarily relate in general to degassing of solvents for liquid chromatography, it will be recognized that other embodiments of the method have application for vacuum degassing of other types of liquids.

The invention claimed is:

1. A method for vacuum degassing of a liquid, the method comprising:
    modulating application of a vacuum to a fluid channel of a degasser so that, for a plurality of volumes of a liquid drawn from the degasser, each volume of the liquid being drawn from the degasser during a pump intake stroke of a pump and having a residence time that is equal to a residence time of each of the other volumes of the liquid, the residence time for each of the volumes of the liquid being responsive to a time that the volume of the liquid resides in the fluid channel under application of the vacuum and to a magnitude of the vacuum.

2. The method of claim 1 wherein the residence times of the volumes of liquid are proportional to a flow rate of the liquid.

3. The method of claim 1 wherein the residence times of the volumes of the liquid are proportional to a frequency of the pump intake strokes.

4. The method of claim 1 wherein the liquid comprises a chromatography solvent.

5. The method of claim 1 wherein modulating application of the vacuum comprises a binary modulation of the vacuum between two fixed pressure levels.

6. The method of claim 5 wherein one of the fixed pressure levels is atmospheric pressure.

7. The method of claim 5 wherein the binary modulation comprises modulating a duration of the vacuum applied to the fluid channel of the degasser.

8. The method of claim 1 wherein modulating application of the vacuum comprises applying the vacuum for a fixed duration before each initiation of a pump intake stroke.

9. The method of claim 1 wherein modulating application of the vacuum comprises applying the vacuum for a duration before each initiation of a pump intake stroke, the duration for each initiation being responsive to a pump stroke volume of a respective one of the pump intake strokes.

10. The method of claim 9 wherein the pump draws volumes of liquid from a plurality of degassers and wherein modulating application of the vacuum comprises applying a vacuum to the fluid channel of each of the degassers before each initiation of a pump intake stroke, the duration for each initiation being responsive to a volume contribution of the respective liquid to the pump stroke volume of the respective one of the pump intake strokes.

11. The method of claim 1 wherein modulating application of the vacuum comprises an analog modulation of vacuum level for a continuously applied vacuum.

12. A system for vacuum degassing of a liquid, comprising:
a plurality of degassers each having a fluid channel to conduct a liquid;
a vacuum source in communication with the plurality of degassers and configured to apply a vacuum to the fluid channel of each of the degassers;
a pump in fluidic communication with the plurality of degassers; and
a processor configured generate a control signal to modulate the application of the vacuum to the fluid channel of one of the degassers, wherein, for a plurality of volumes of a liquid drawn from one of the degassers, each volume of the liquid has a residence time that is equal to a residence time of each of the other volumes of the liquid, the residence time for each of the volumes of the liquid being responsive to a time that the volume of the liquid resides in the fluid channel under application of the vacuum and to a magnitude of the vacuum and wherein the control signal is responsive to a volume contribution of the liquid from the one of the degassers to a total volume of liquid acquired by the pump during a pump intake stroke.

13. The system of claim 12 wherein the liquid is a chromatography solvent.

14. The system of claim 12 wherein the control signal controls a binary modulation of the applied vacuum.

15. The system of claim 12 wherein the control signal controls an analog modulation of the magnitude of the applied vacuum.

16. The system of claim 12 wherein the control signal is responsive to a flow rate of the liquid.

17. The system of claim 12 wherein the control signal is responsive to a frequency of pump strokes of the pump.

* * * * *